United States Patent
Nomura et al.

(10) Patent No.: US 7,037,353 B2
(45) Date of Patent: May 2, 2006

(54) MINUS ION GENERATING APPARATUS, MINUS ION GENERATING SYSTEM, AND MINUS ION GENERATING METHOD

(75) Inventors: Shuzo Nomura, Kanagawa (JP); Keizo Kitajima, Tokyo (JP)

(73) Assignee: Nomura Reinetsu Yugensgaisha, Kanagawa-ken (JP)

( * ) Notice: Subject to any disclaimer, the term of this patent is extended or adjusted under 35 U.S.C. 154(b) by 175 days.

(21) Appl. No.: 10/451,424

(22) PCT Filed: Dec. 25, 2001

(86) PCT No.: PCT/JP01/11350

§ 371 (c)(1),
(2), (4) Date: Dec. 10, 2003

(87) PCT Pub. No.: WO02/052203

PCT Pub. Date: Jul. 4, 2002

(65) Prior Publication Data

US 2004/0109279 A1    Jun. 10, 2004

(30) Foreign Application Priority Data

Dec. 25, 2000    (JP)    .............................. 2000-404515

(51) Int. Cl.
*B01D 50/00*    (2006.01)
(52) U.S. Cl. .................. 55/385.1; 239/558; 96/355
(58) Field of Classification Search ............... 55/385.1; 96/355; 239/558; 361/227; 366/336
See application file for complete search history.

(56) References Cited

U.S. PATENT DOCUMENTS 3,785,779 A * 1/1974 Li et al. ...................... 422/231
6,730,214 B1 * 5/2004 Mazzei ........................ 210/188

* cited by examiner

*Primary Examiner*—Robert A. Hopkins
(74) *Attorney, Agent, or Firm*—Sughrue Mion, PLLC

(57) ABSTRACT

This is a minus ion generating apparatus by which cluster ions in which minus ions and plus ions are mixed can be readily and largely fabricated and only minus ions can be separated and used. The apparatus is characterized in that a spray nozzle is connected to a gas-and-liquid separator. In order to more effectively generate the minus ions, the minus ion generating apparatus comprises a mixing flow path, a supplying flow path for fluid and a discharging flow path for fluid which are in communication with the mixing flow path. The mixing flow path comprises plural circular flow paths that are arranged in parallel and that are communicated in a radial direction; plural inlets and plural outlets formed in circular flow paths, so that the location of the inlets and the location of the outlets are mutually different in a radial direction; plural communicating flow paths by which the inlets formed in one circular flow path communicates with the outlets formed in another circular flow. The spray nozzle is connected to a supplying flow path and the gas-and-liquid separator is connected to a discharging flow path. A minus ion generating system is characterized in that plural ion generating apparatuses are connected to pipes for sending wind in a single system.

9 Claims, 12 Drawing Sheets

Distance Measured from Minus Ion Generation Apparatus

MINUS ION GENERATING APPARATUS, MINUS ION GENERATING SYSTEM, AND MINUS ION GENERATING METHOD

TECHNICAL FIELD

The present invention relates to a minus ion generating apparatus, a minus ion generating system and a minus ion generating method.

BACKGROUND ART

As for minus ion generating methods, a minus ion generating method has been designed, in which an artificial fall is installed in a space, thereby mist is generated mechanically, taking notice of "Lenard effect" by which a large number of minus ions exist in the vicinity of a fall. Further, the other minus ion generating method has been designed, in which wind transported by a blower is used and a centrifugal force is used, thereby fine mist is produced, resulting in that minus ions are generated. Furthermore, a corona discharge method has been designed, thereby minus ions are electrically generated.

According to the above-mentioned method in which an artificial fall is installed in the room, thereby fine mist is generated, resulting in that minus ions are generated in the air, a particle of water drop broken in the vicinity of the fall is too large to become a small particle of water drop, resulting in that generation of the minus ion is restricted. Also, a particle of water to be fined is still large in the vicinity of the fall, therefore it can be recognized that plus ions are generated. According to the method, a large amount of water must be circulated and flown simultaneously, and vast cost of equipment is required concerning cost.

According to the above-mentioned method in which the centrifugal force of wind transported by the blower or the like is used, thereby fine mist is produced, resulting in that minus ions are generated, likewise, a particle of water is not be sufficiently fined, resulting in that a large number of plus ions are generated, and a number of minus ions are not sufficiently generated. Simultaneously, therein, much drain is generated.

In any of the above-mentioned methods, the particle of water to be generated is still large, resulting in that there exist a large number of plus ions and there are a small number of minus ions to be generated.

According to the above-mentioned method using the corona discharge phenomenon in which minus ions are electrically generated, not only the minus ions but also plus ions are simultaneously generated, and further a period between appearance and disappearance of minus ions is short, resulting in that there occurs a practical problem. Additionally, ozone and nitro-oxide are generated. There is a fear that a harmful gas might occur owing to dirty of electrodes. Also, it is difficult to always stabilize discharging state, so that the minus ions cannot be stably and safely generated.

In any of the above-mentioned methods, minus ions are being produced, while plus ions are being generated. Therefore, an effect of minus ions has been reduced.

DISCLOSURE OF INVENTION

In order to solve the above-mentioned problems, the present invention provides a minus ion generating apparatus characterized in that a gas-and-liquid separator is connected to a spray nozzle.

Further, a minus ion generating apparatus of the present invention may comprise:
mixing flow path comprising:
plural circular flow paths that are arranged in parallel and that are communicated in a radial direction,
plural inlets and plural outlets formed in said circular flow paths so that the location of the inlets and the location of the outlets are mutually different in a radial direction in each of said circular flow paths,
plural communicating flow paths by which the inlet formed in one circular flow path communicates with the outlet formed in another circular flow path, and
a supplying flow path for fluid and an discharging flow path for fluid which communicate with the mixing flow path.

A tank may be connected to the supplying flow path and/or the discharging flow path.

Preferably, a spray nozzle is connected to the supplying flow path and/or the gas-and-liquid separator is connected to the discharging path.

Preferably, a device that supplies air such as a blower for supplying air and an air compressor is connected to the supplying flow path, and a device that supplies water is connected to the supplying flow path.

A minus ion generating system may be provided in which the minus ion generating apparatus are connected to a pipe for sending wind in a single system manner at plural locations.

A minus ion generating method may be provided in which minus ions are generated by sending water and air to the minus ion generating apparatus and the minus ion generating system.

According to the present invention that is constructed as above-mentioned, minus ions are generated when water in the air is scattered in the spray nozzle or owing to collision-turbulent-flow movement of the high-speed air in the flow paths by sending the air mixed with water.

As means for mixing water with air, using of the spray nozzle allows water to be supplied in a sprayed state. Also, if water is absorbed up and is supplied by using siphon phenomenon, then a pump for pressurizing and supplying water can be omitted.

Preferably, the gas-and-liquid separator is provided on the discharging flow path, mist in the air is made into condensed water, and the condensed water is separated from the air. The gas-and-liquid separator is a drain separator, a drain catcher, and the like.

In the invention according to claim 9, minus ions are generated by plural minus ion generating apparatuses using air transported from the pipe for sending wind.

The present invention is constituted as mentioned above and a large amount of minus ions can be readily generated. Further, in the constitution where the gas-and-liquid separator is provided, mist in the air can be separated from released air, and simultaneously plus ions can be separated.

In the invention according to claim 9, minus ions can be generated at plural locations.

BRIEF DESCRIPTION OF DRAWINGS

FIG. 11 shows an external mixing type spray nozzle and FIG. 12 shows an internal mixing type spray nozzle.

Figure 1:
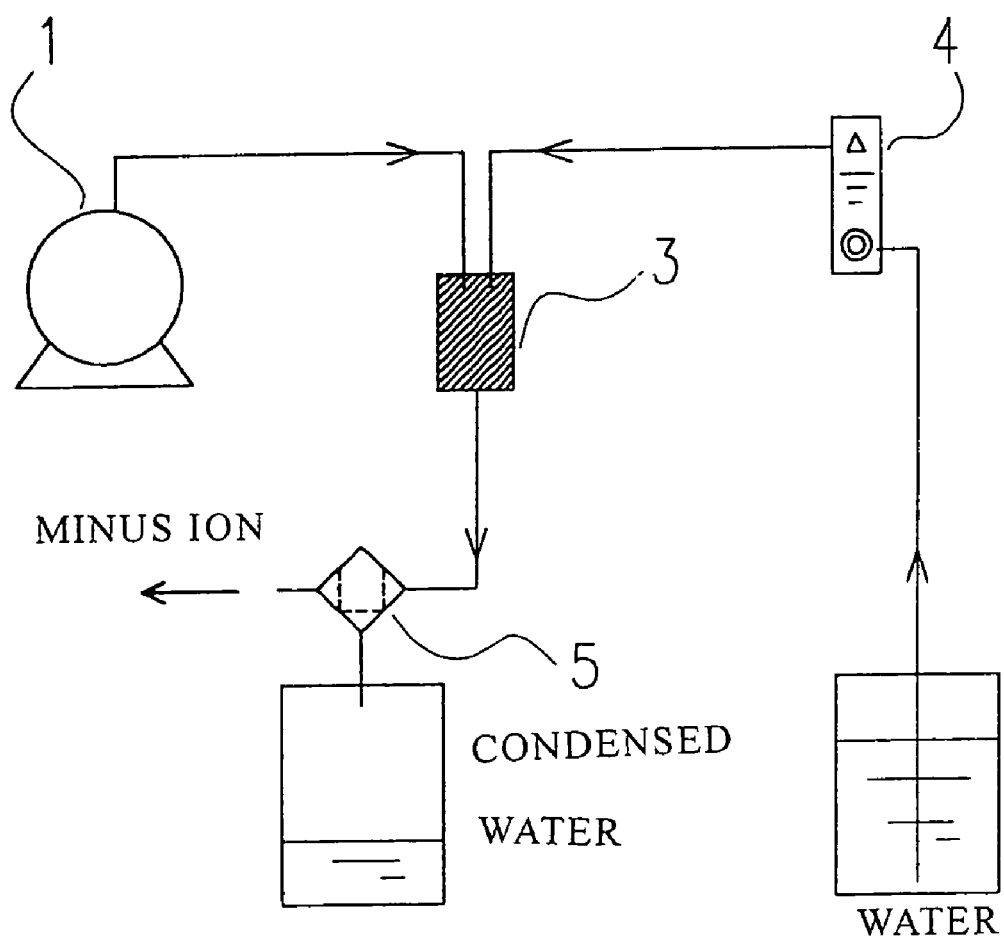
FIG. 1 is a schematic view of one embodiment of a minus ion generating apparatus according to the present invention.

Explanations of numerals used in drawings will be as follows;

1 Compressor
1' Blower
2 Mixer
3 Spray Nozzle
3' Water Adjusting Valve
4 Flow Meter
5 Gas-and-liquid Separator (Drain Separator, Drain Catcher, or the like)
6 Pipe for Sending Wind
A Minus Ion Generating Apparatus comprising the above components corresponding to numerals 2, 3, 4 and 5
B Minus Ion Generating Apparatus comprising the above components corresponding to numerals 3, 4 and 5
21 Mixing Flow Path
22 Supplying Flow Path
23 Discharging Flow Path
24 Circular Flow path
25 Communicating Flow Path
26 Tank at the Supplying Side
27 Tank at the Discharging Side
28 Inlet
29 Outlet
51 Member
52 Member
53 Member
54 Member
55 Member
56 Member
57 Member
58 Member
61 External Container
62 Internal Container
63 Pipe
64 Pipe

BEST MODE FOR CARRYING OUT THE INVENTION

Hereinafter, it will be explained about the mode for carrying out the invention, referring to the drawings.

FIG. 1 is a schematic view of a minus ion generating apparatus in which a spray nozzle and a gas-and-liquid separator are combined, an absorbing force generated in case of supplying an air is used, water is absorbed using siphon phenomenon, sprayed water is discharged and cluster ions are generated, and condensed water and air are separated by the gas-and-liquid separator, resulting in that selective separation such that minus ions exist in the air while plus ions exist in the water is can be performed. Components 1, 3, 4 and 5 constituting the apparatus are connected by using pipes. A pipe is set at an exit of the spray nozzle so as to have a slight space and the other end of the pipe is connected to the gas-and-liquid separator. In a case where the pipe is set at the exit of the spray nozzle, the pipe may be set in a sealing manner at the exit of the spray nozzle without any space between the pipe and the exit.

There are a one-fluid-type nozzle and a two-fluid-type nozzle as a spray nozzle. The two-fluid-type nozzle is here used. The two-fluid-type nozzle is a nozzle that changes fluid into fine particles by using a high-speed flow of pressurized air and has a more splendid fine particle producing capability and the like than the one-fluid-type nozzle that performs spray operation only using the pressurized liquid.

Figure 11:
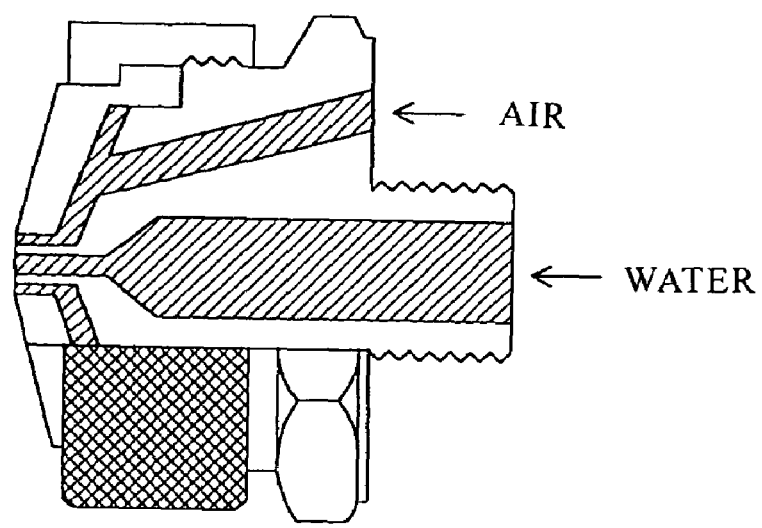
FIG. 11 and FIG. 12 are respectively sectional views of a spray nozzle used for the embodiments of the present invention.
Figure 12:
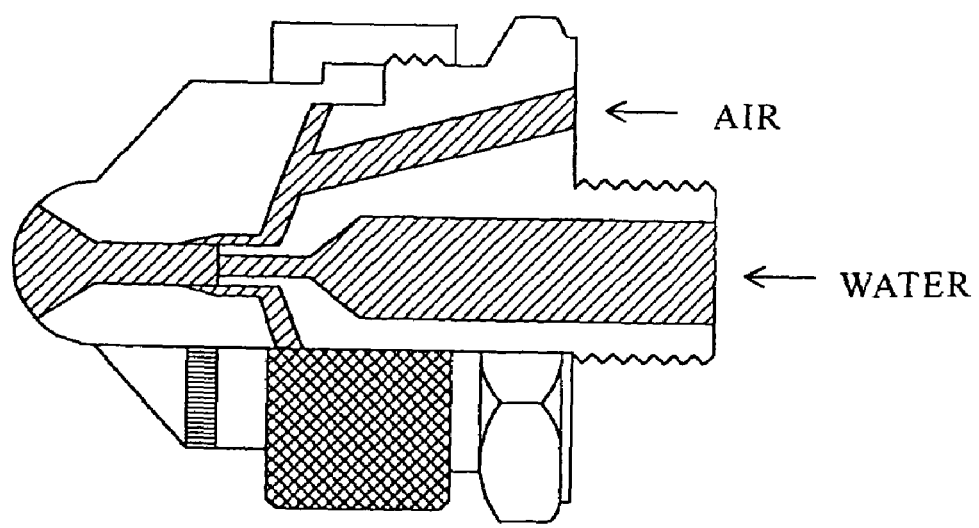

According to the two-fluid-type nozzle, as shown in FIG. 11 and FIG. 12, a pressurized air is supplied from an opening for supplying air, liquid is supplied from an opening for supplying liquid, the air and the liquid are mixed at an external portion of tip of the nozzle (see FIG. 11) or an internal portion of tip of the nozzle, resulting in that the mixed air and liquid are discharged as a fine particle producing spray. As a method of supplying liquid, there exist a method of supplying pressurized liquid; a method in which a siphon tube inserted into a tank containing liquid is connected to an opening for supplying liquid of the spray nozzle, the pressurized air passes through the spray nozzle, resulting in that liquid is absorbed up using a principle of siphon; and a method of performing supply operation by gravity.

Figure 13:
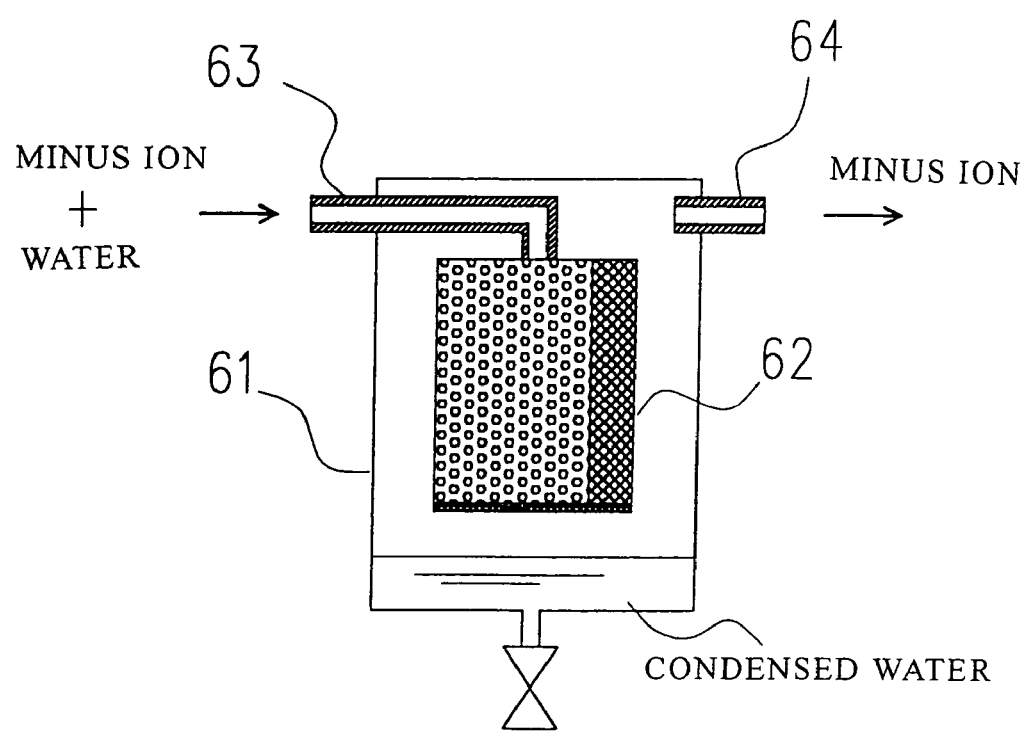
FIG. 13 is a schematic view of a gas-and-liquid separator used in the embodiment of the present invention.

The gas-and-liquid separator is for separating gas such as air or the like and liquid such as water or the like. There exist various kinds of gas-and-liquid separators, and a typical one is a drain separator used for mainly removing water under a high-pressurized air. There exists a drain catcher as an apparatus used for removing a large amount of water. In the drain catcher, as shown in FIG. 13, a pipe 63 that introduces mixing of gas and liquid is connected to a cylindrical internal container 62 having a large number of small holes, and a pipe 64 that discharges gas obtained by removing water component is provided at an external container 61 that covers the internal container. When air including minus ions which is mixed with water is introduced to the drain catcher, water particles collide against an internal surface of the container, the collided water particles are changed into liquid drops which fall down, and air including minus ions from which the water has been removed is discharged from the exit of the pipe 64.

Figure 2:
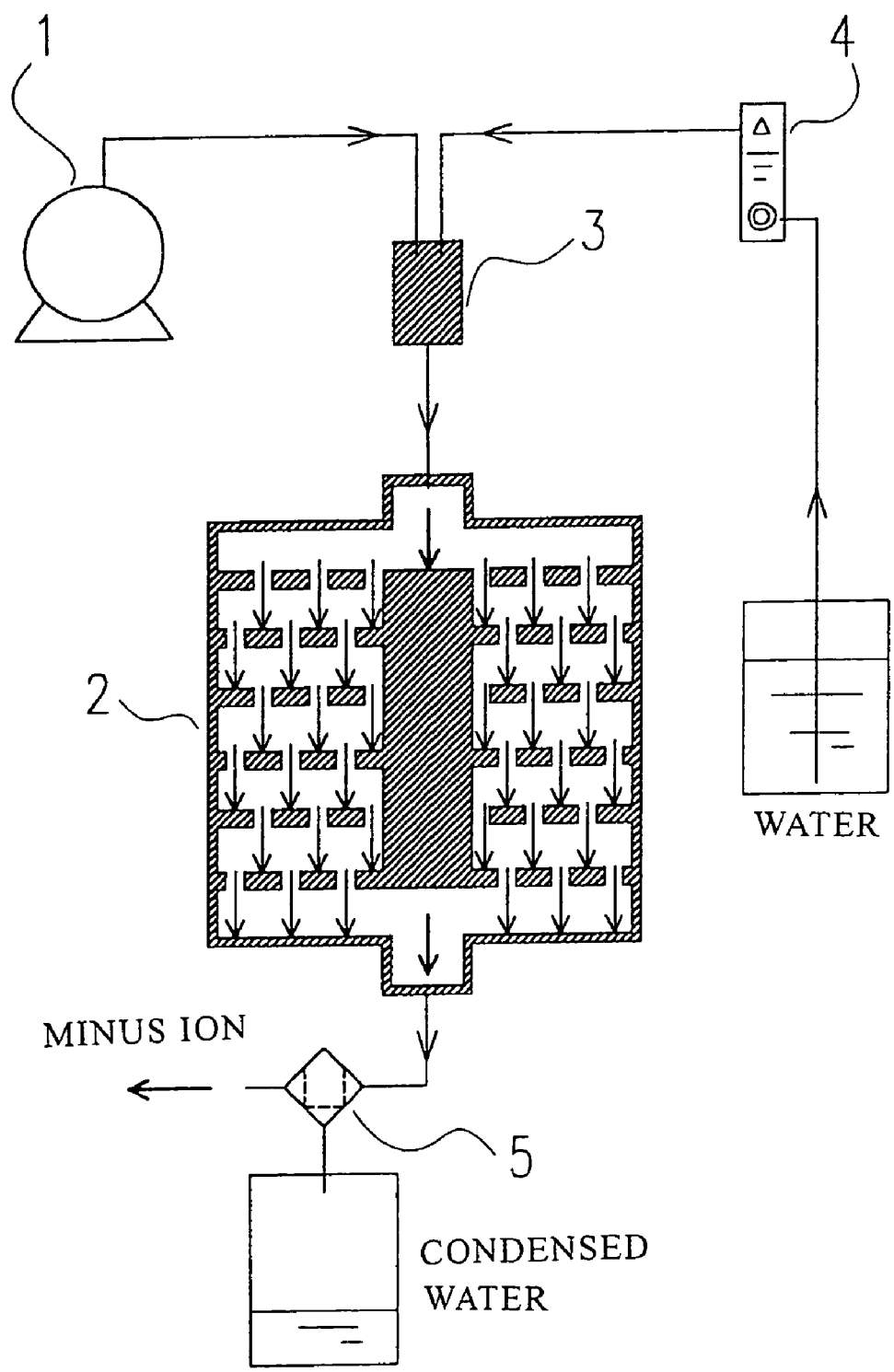
FIG. 2 is a schematic view of the other embodiment of a minus ion generating apparatus according to the present invention.

FIG. 2 is a schematic view of a minus ion generating apparatus in which a spray nozzle and a mixer are combined, an absorbing force generated in case of supplying air is used, water is absorbed by siphon phenomenon, sprayed water is discharged and cluster ions are generated, a large number of minus ions can be generated by using a mixer, and condensed water and air are separated by using a gas-and-liquid separator, resulting in that selective separation such that minus ions exist in the air and plus ions exist in the water is performed. Components 1, 2, 3, 4, and 5 constituting the apparatus are connected by way of pipes.

Figure 3:
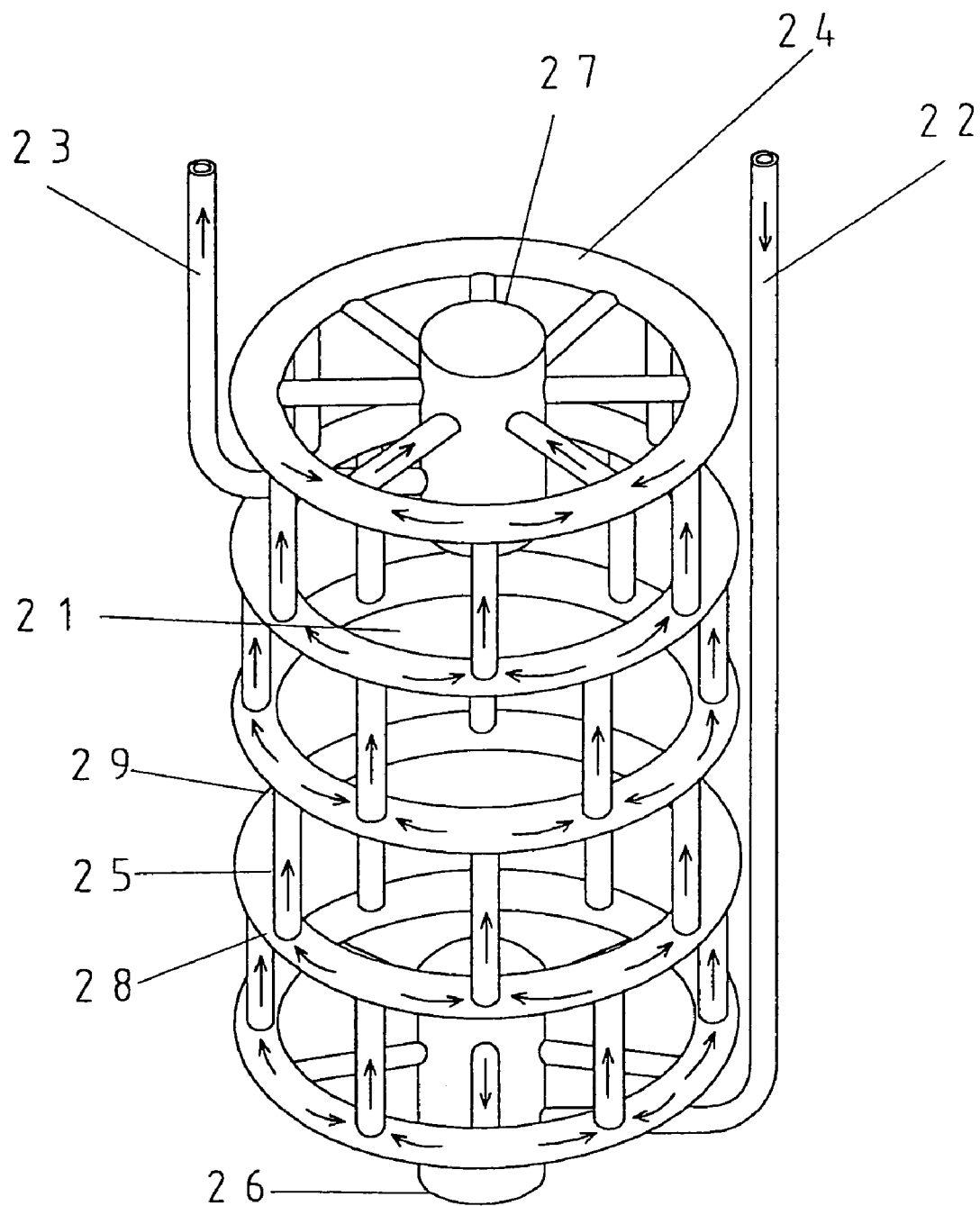
FIG. 3 is a perspective view in a case where a mixing flow path used for one embodiment of the minus ion generating apparatus according to the present invention is made in a pipe manner.

FIG. 3 is a perspective view in a case where a mixing flow path used for the apparatus of one embodiment of the present invention is made in a pipe manner.

The mixer 2 is provided with same flow paths as used in a heat-exchanging apparatus disclosed in Japanese Patent Laid-open Application (JP HEI 7-294162) Gazette. The mixer 2 in the present embodiment comprises a mixing flow path 21, a supplying pipe 22 that supplies a mixing gas of air and water, and a discharging pipe 23 for discharging. The mixing flow path 21 comprises circular flow paths 24, communicating flow paths 25, a tank 26 for introducing a mixed gas from the supplying flow path 22 to the communicating flow paths 25, and a tank 27 for introducing the mixed gas from communicating flow paths 25 to the discharging flow path 23. The number of the circulating paths may be a desired number of two or more. Also, the number of the communicating flow paths may be a desired number of two or more. As for the embodiments of the present invention, in the embodiment relating to FIG. 3, five circular flow paths and six communicating flow paths are used. In the embodiment relating to FIG. 4, two circular flow paths and six communicating flow paths are used.

Pipe members are, for example, made of metal, plastic, ceramic or the like.

A high-speed fan, a blower, a compressor or the like are used as means for supplying a high-speed air to the spray nozzle.

When the high-speed air is transported to the spray nozzle, water is absorbed up by using siphon phenomenon caused by airflow speed in case of transporting high-speed air, resulting in that the water is sprayed and transported.

In case of FIG. 1, a proper amount of water is transported by way of a flow meter 4 for water into the high-speed air to be transported to the spray nozzle 3 from a compressor 1. Thereafter, the water is sprayed and finely misted by the spray nozzle 3 and is mixed into the gas-and-liquid separator 5. Fined mist in the air is condensed within the gas-and-liquid separator 5 by lowering of temperature owing to adiabatic expansion movement of air caused by the spray nozzle 3, resulting in that the fined mist become water drops. Therefore, water in the air can be separated from air by the gas-and-liquid separator 5.

In case of FIG. 2, a proper amount of water is transported by way of the flow meter 4 for water into the high-speed air to be transported to the spray nozzle 3 before the spray nozzle 3. Thereafter, the water is sprayed and finely misted by the spray nozzle 3 and is mixed into the mixing flow path 2. The mixed air of the high-speed air and the finely misted water enters a tank 26 at a supplying side from supplying flow path 22. The mixed air that has collided within the tank 26 enters a circular flow path 24 lying at a first stage from outlets 29 by way of inlets 28 of plural communicating flow paths 25 connected to the tank 26 at the supplying side. Thereafter, the mixed air collides against a wall surface of the circular flow path 24. Further, the airs mixed with water which entered from different inlets mutually collide.

Likewise, the high-speed air mixed with water enters the circular flow path 24 lying at a second stage from outlets 29 by way of inlets 28 of plural communicating flow paths 25 connected to the circular flow path 24 lying at the first stage. Thereafter, the high-speed air mixed with water collides against a wall surface of the circular flow path 24 and the mixed airs which entered from different inlets mutually collide. Next, the mixed air enters a tank 27 from outlets 29 by way of inlets 28 of plural communicating flow paths 25 connected to a circular flow path 24 lying at a final stage. The mixed air that has collide against an inner surface of the tank 27 is discharged from a discharging flow path 23. Owing to lowering of temperature by adiabatic expansion movement of air caused by the spray nozzle 3 and lowering of temperature by collision-and-turbulent flow movement of air within the mixing flow path 21, fined mist in the air is condensed to be water drops. As a result, if the gas-and-liquid separator 5 is provided at the discharging flow path 23, water in the air can be separated from the air.

In case of FIG. 1, the water in the air sprayed by the spray nozzle certainly generates minus ions, but includes a large amount of plus ions because particles of water has been still large. Then, if the gas-and-liquid separator is provided at the exit of the spray nozzle, water in the air can be separated from the air, resulting in that it can be prevented that water in the air is released toward an environmental space. At the same time, plus ions whose particle is larger than the particle of minus ions, are also separated together with the water, so that an effect of generation of minus ions to be released from the exit of the gas-and-liquid separator 5 can be enhanced. Then, the minus ions are bonded to water molecules which have been fined in the air, so that such minus ions exist under a stable state, and high-speed air including only a large amount of minus ions is discharged from the gas-and-liquid separator 5.

In case of FIG. 2, the water in the air that has been sprayed by the spray nozzle generates minus ions, but particle of the water has been still large, so that the water includes a large amount of plus ions.

Next, water in the air in which a large amount of minus ions and plus ions are mixed collides against the inner wall surface of the tank 26 and the wall surface of the circular flow path 24. Simultaneously, when airs mixed with water that entered from different inlets mutually collide, the above water in the air is more finely broken and becomes fine mists and is scattered. Then, hydrogen boding of the water is broken, so that the water is charged by minus electric charge. Therefore, the air further includes more amount of minus ions.

The high-speed mixed air collides against wall surfaces at plural locations in the circular flow path 24 and performs collision-turbulent-flow movement, so that water in the mixed air further becomes finer, resulting in that the water becomes very fine particle. Therefore, the minus ions are mutually bonded, thereby they exist in a stable state.

When the high-speed air passes through the mixing flow path 21, temperature of the air is lowered owing to the collision-turbulent-flow movement within the flow path. Therefore, finely misted water in the air whose particle is large is condensed to be water drops. Then, the gas-and-liquid separator is provided at the discharging flow path, thereby the condensed water to be generated is separated from the air, resulting in that it can be prevented that the condensed water is released toward an outside space. Then, because plus ions whose particle is larger than the particle of minus ions is also separated together with the condensed water, an effect of generation of the minus ions to be released from the exit of the discharging flow path 23 can be enhanced. Then, minus ions are bonded to water molecules which have become fine in the air, so that the minus ions can exist under a stable state and the high-speed air including a large amount of minus ions is discharged from the discharging path 23.

According to the method of scattering water owing to a once falling of water in a fall or the method of spraying only using a spray nozzle, each of particles of the water has been still large and there have still existed a large number of plus ions. On the contrary, according to the present apparatus, a large amount of fine water particles can be generated more efficiently than known methods such as the above-mentioned minus ion generating method of generating minus ions when water is scattered owing to once falling of water in a fall and a method of generating fine mist by using a centrifugal force caused by sending wind of a blower or the like and generating minus ions. As a result, according to the present invention, a large amount of minus ions can be generated.

Also, a necessary amount of consumed air can be saved in order to change water into fine mist by using the spray nozzle.

Simultaneously, the gas-and-liquid separator such as a mist separator, a drain catcher or the like is provided at the discharging flow path, thereby fine mist in the air can be condensed to be water drops and be separated from releasing air without any cooling device, by temperature lowering within the mixing flow path to be generated by the adiabatic expansion of the high-pressurized air by using the spray nozzle and the collision-turbulent flow movement within the mixer.

The minus ions that have been separated from condensed water and bonded to water molecules that have been fine and exist under a stable state, are discharged together with the high-speed air toward an available space, resulting in that minus ions are scattered toward a wide space.

The separated and condensed water is separated and recovered into a container or toward an outside space, resulting in that release of the separated and condensed water toward an available space can be prevented. Then, also plus ions whose particles are large are separated together with the condensed water, so that only minus ions can be released from the exit of the gas-and-liquid separator and an effect of generation of minus ions can be enhanced.

According to the above-mentioned embodiment, there is no fear that harmful gas might be produced owing to dirty of electrodes in the minus ion generating method employing corona discharging. Namely, only a large number of minus ions can be effectively, safely and stably generated, by spraying operation of the spray nozzle, or by spraying operation of the spray nozzle and allowing a small amount of water included in the high-speed air within the mixer to be repeatedly moved based on the collision-and-turbulent flow movement.

Figure 6:
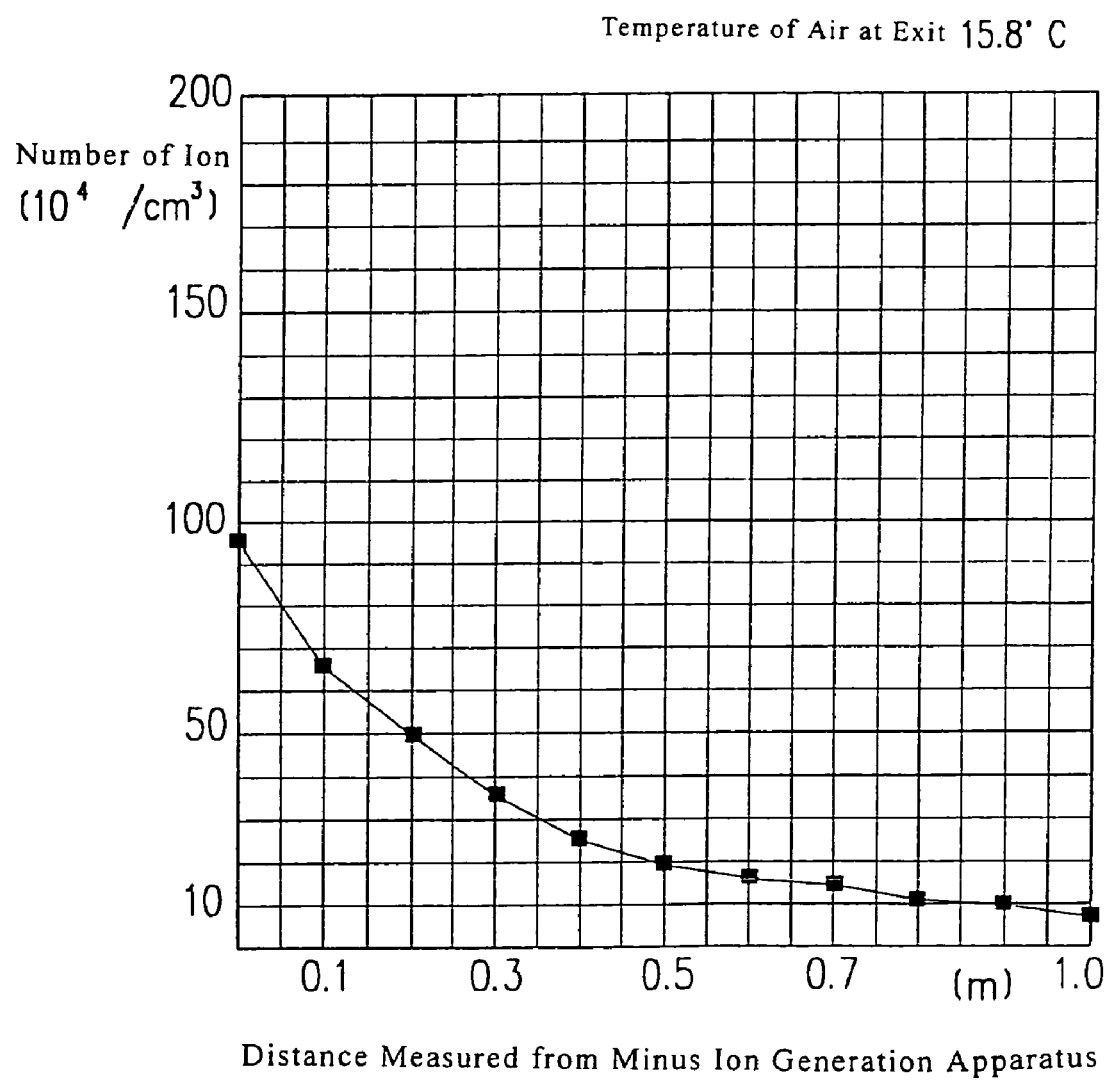
FIG. 6 is a graph representing an experimental result of an amount of minus ions being generated using one embodiment of the minus ion generating apparatus according to the present invention.
Figure 7:
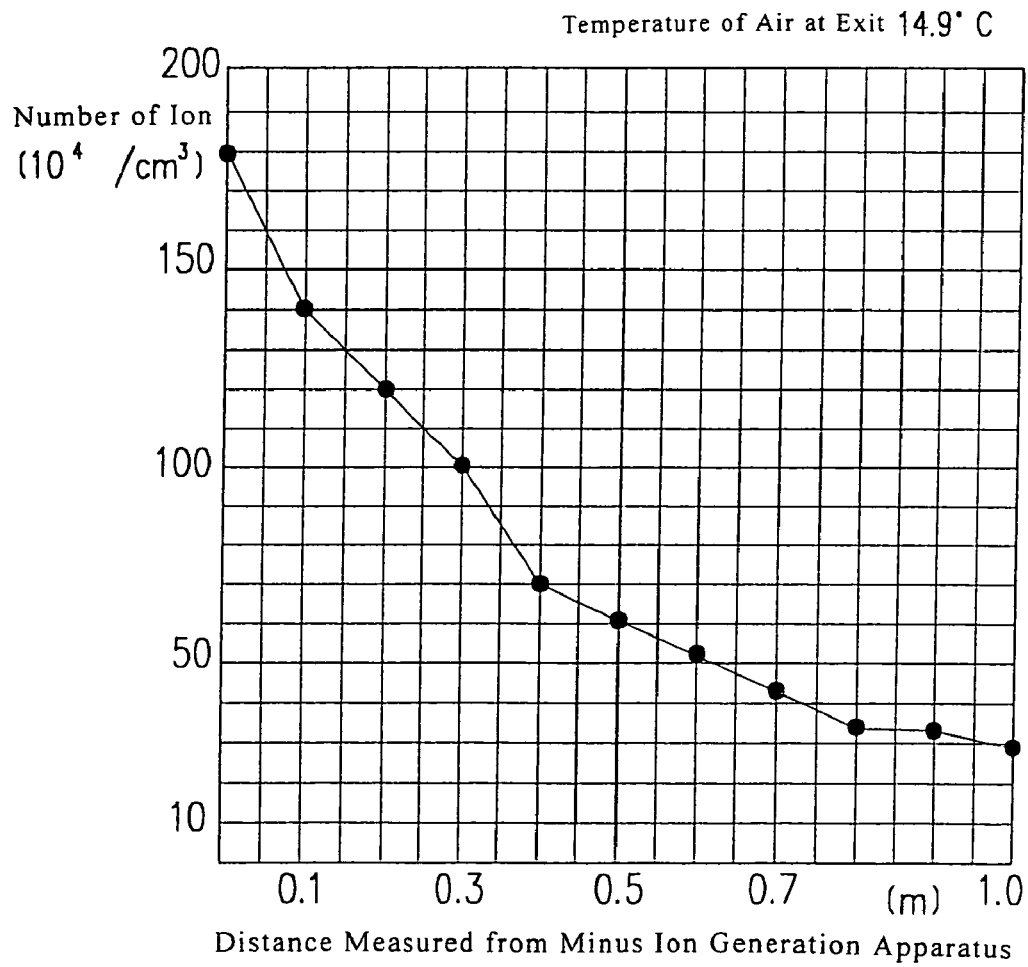
FIG. 7 is a graph representing an experimental result of an amount of minus ions being generated using the other embodiment of the minus ion generating apparatus according to the present invention.

Through the above-mentioned constitution, in the present embodiments, as shown in FIG. 6 and FIG. 7, splendid performance can be attained.

In the performed experiment, in a case of the constitution of FIG. 1, when a pressurized air by a compressor whose pressure was 5 [kg/cm$^2$] was used by the amount of 12 [liter/min], if a constant amount of water whose amount was 2.0 [cc/min] was mixed to the air, as shown in FIG. 6, at the exit of the gas-and-liquid separator 5, minus ions were generated by 960,000 [ions/cm$^3$], and at a location where the distance from the minus ion generating apparatus was 1 [meter], minus ions were generated by 89,000 [ions/cm$^3$]. Lowering of temperature of the air by the adiabatic expansion movement was 6.8 [° C.]. In this experiment, "AM12" manufactured by ATOMAX Inc. was used as the spray nozzle, and "Drain Catcher AMG150" manufactured by SMC Co. was used as the gas-and-liquid separator (They were also used in the constitution of FIG. 2.).

Further, at the exit of the gas-and-liquid separator, the generation of plus ions could not be detected at all. The generating condensed water can be safely recovered within the container or toward any exterior environment without being released toward the available space, using the gas-and-liquid separator such as a mist separator and a drain catcher.

In a case of the constitution of FIG. 2, when a pressurized air by a compressor whose pressure was 5 [kg/cm$^2$] was used by the amount of 12 [liter/min], if a constant amount of water whose amount was 2.0 [cc/min] was mixed to the air, as shown in FIG. 7, at the exit of the gas-and-liquid separator 5, minus ions were generated by 1,800,000 [ions/cm$^3$], and at a location where the distance from the discharging flow path 23 of the minus ion generating apparatus was 1 [meter], minus ions were generated by 280,000 [ions/cm$^3$]. This result meets a condition under International Ionization Standard (in which 100,000 [ions/cm$^3$] or more must be measured at a location of 1 [meter] from the apparatus). Lowering of temperature of the air by the adiabatic expansion movement and collision-and-turbulent flow movement was 9.9 [° C.].

Further, at the exit of the gas-and-liquid separator, the generation of plus ions could not be detected at all. The condensed water in the mixing flow path can be safely recovered in the container or toward outside of the room without being released toward an available space by using the gas-and-liquid separator such as a mist separator and a drain catcher.

Figure 4:
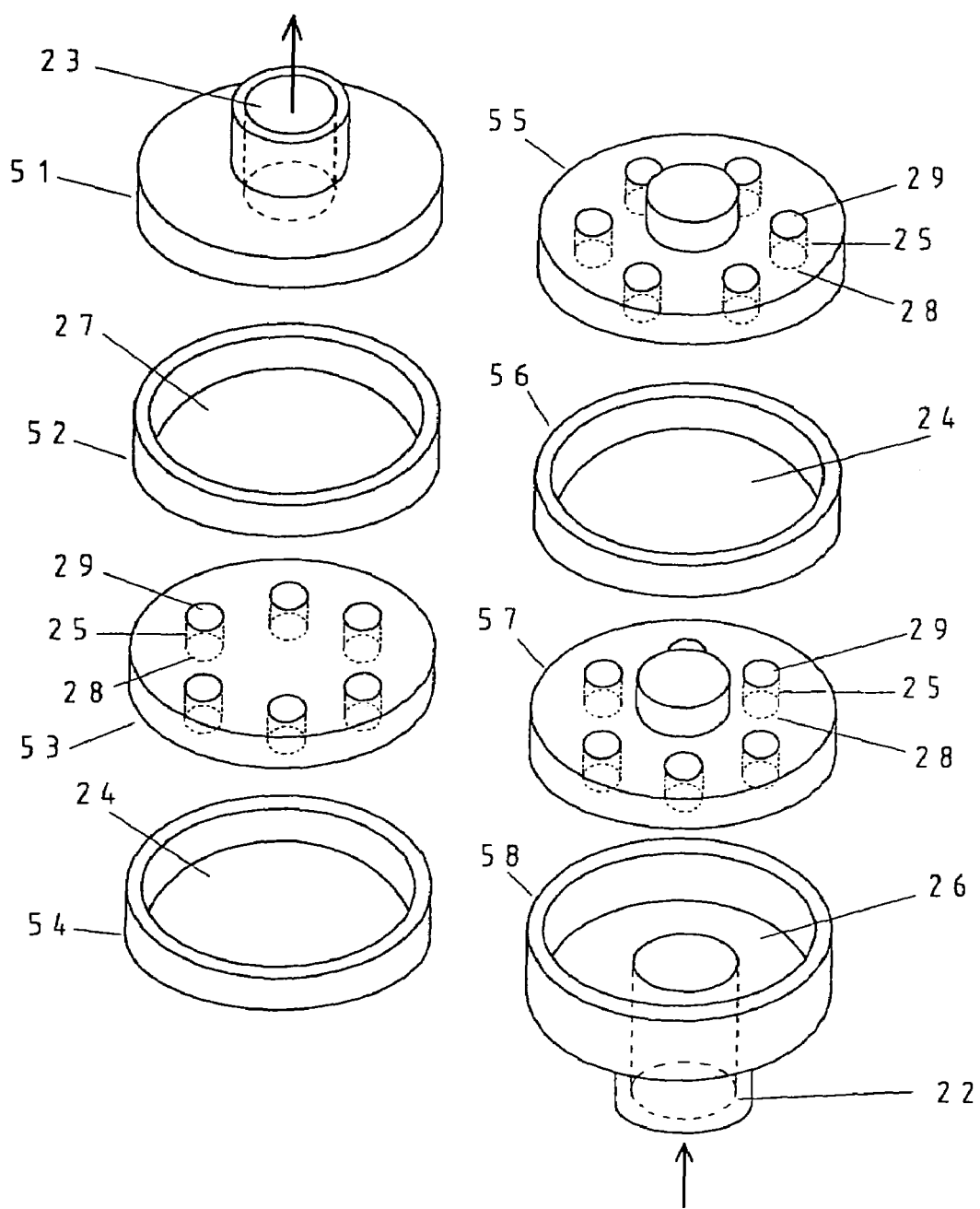
FIG. 4 is a perspective view in a case where a mixing flow path used for one embodiment of the minus ion generating apparatus according to the present invention is made in a block manner.

FIG. 4 shows a mixing flow path used for a minus ion generating apparatus in one embodiment of the present invention, which is made in a block manner In FIG. 4, a heat exchanging flow path is fabricated by coupling working from a member 51 to a member 58 in order. The members 54, 56 are cylindrical shown in FIG. 4. Neighboring members 55, 57 to the members 54, 56 have a convex portion in the center of each of members 55, 57. By coupling them with the other neighboring member, circular flow paths 24, 24 are formed. A communicating flow path 25 having inlets 28 and outlets 29 are provided in the members 53, 55 and 57. A tank 26 at a supplying side is formed by coupling the members 57, 58 and a tank 27 at a discharging side is formed by coupling the members 51, 52 and 53. Needless to say, the supplying side and the discharging side can be exchanged.

In this embodiment, flow paths are formed by engraving material such as ceramic, plastic or metal, by cooling and hardening fluid body such as casting material, plastic and glass except only space portions to be flow paths using a mold, or by pressing and hardening, drying or sintering fluid body such as ceramic except only space portions to be flow paths.

Thereby, the apparatus of this embodiment can be mass-produced, and further fabricated by low cost.

Figure 5:
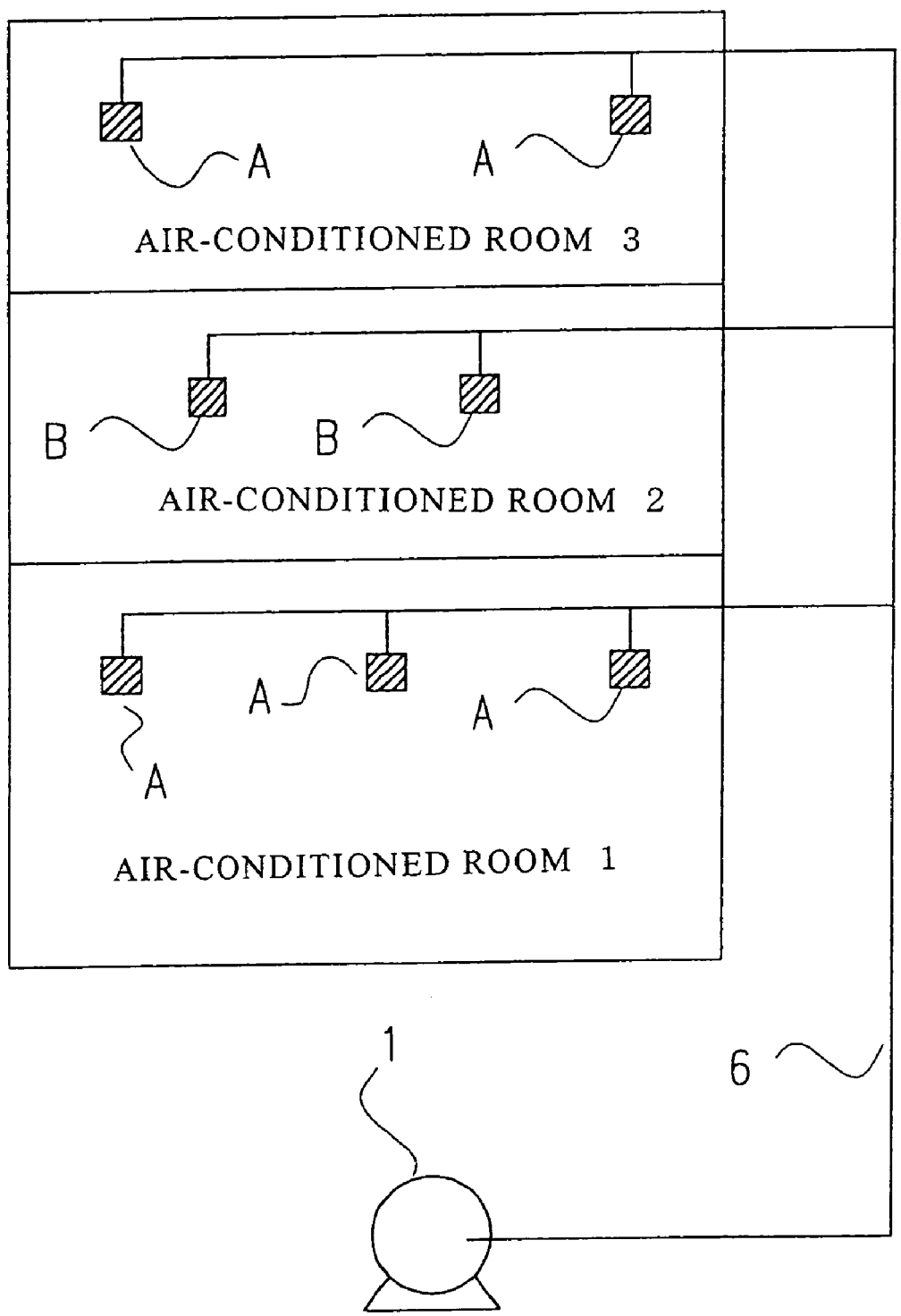
FIG. 5 is a schematic view of a system in which minus ion generating apparatuses are provided at plural locations and air is supplied by a pipe for sending wind, resulting in that minus ions can be simultaneously generated at plural locations using a single compressor.

FIG. 5 shows the embodiment of the present invention employing a system characterized in that the minus ion generating apparatuses having the constitution shown in FIG. 1 or FIG. 2 are arranged at plural locations, air generated by a single compressor is supplied by way of sending pipes, so that minus ions can be simultaneously generated at plural locations.

Based on the property of minus ion, minus ions are spread over from one area where the ion density of minus ions is thick to other area where the ion density is thin, resulting in that a state of existence of minus ions gradually becomes even. Together with time elapse, in other words, with longer distance from the minus ion generating apparatus, minus ions are spread over.

Therefore, in order to enhance the effect caused by minus ions, the apparatus can produce more splendid effect by providing the apparatus within a partitioned space rather than an opened space. Additionally, the apparatus can produce more splendid effect by providing the apparatus by plural numbers within the same room.

On the other hand, it is most desirable that there exist only minus ions in a sealed space while there is no plus ion.

Therefore, in order to simultaneously generate minus ions at many room spaces, the minus ion generating apparatuses are required, whose number is equal to or more than the number of the room spaces. Here, by providing a compressor at outside of the room and providing openings for supplying air in each of the rooms using sending pipes, a single compressor can simultaneously generate minus ions at plural locations of plural room spaces. Simultaneously, by providing the compressor that will become a source for generating noise and/or vibration at the outside of the room, the inside of the room becomes quieter than conventional.

According to the system of FIG. 4, by providing the compressor at the outside of the room, an effect can be performed that minus ions are simultaneously generated at plural locations in inside of plural rooms using a single compressor without transmitting a noise caused by a compressor to the inside of the room.

It is considerable that the minus ion generating apparatus of the present invention is used not only for such generation of minus ions but also for following usages.

If water including impurities such as seawater or the like is injected into the apparatus of the present embodiment by using phenomenon that particles of water are fined, the seawater is mixed with an air and thereafter the seawater is fined, while water component whose particle is fine is released together with the air. On the other hand, mist whose particle is large and that includes impurities such as salt component is condensed and water-dropped under a low temperature that occurs within the mixing flow path owing to adiabatic expansion of the air by the spray nozzle and owing to both adiabatic expansion of the air by the spray nozzle and collision-turbulent-flow movement of mixed gas.

If providing a gas-and-liquid separator such as a mist separator and a drain catcher at the spray nozzle or the mixer, then the water drops are separated from the released air, so that efficiency of the apparatus can be further enhanced. Thus, separation can be established between the water and the impurities such as salt component that has been dissolved in the water.

As the other usage, if a medicine in a liquid manner or the like is tranported in place of water in a same manner, then the medicine liquid is made into fine particles, resulting in that the medicine can be spread over in an even state for a short time toward the air (atmosphere). As a result, a space of the room can be sterilized for a short time.

By providing a gas-and-liquid separator such as a mist separator or a drain catcher at the spray nozzle or the mixer, the medicine is condensed and water-dropped under a low temperature that occurs within the mixing flow path owing to adiabatic expansion of the air by the spray nozzle and owing to both the adiabatic expansion of the air by the spray nozzle and the collision-turbulent-flow movement of the mixed gas.

By providing a gas-and-liquid separator such as a mist separator and a drain catcher at the spray nozzle or the mixer, if mist whose particle is large is condensed and condensed mist is separated as water drops, by temperature lowering within the mixing flow path owing to collision-turbulent-flow movement of the mixed gas, then the water drops are separated from the released air, so that efficiency of the apparatus can be further enhanced.

Further, as the other usage, if mixing material of various kinds of liquid is injected to the apparatus of the present embodiment in place of water, then various kinds of liquids can be evenly fined.

By providing a gas-and-liquid separator such as a mist separator or a drain catcher at the spray nozzle or the mixer, the mixing material is condensed and water-dropped under a low temperature occurs within the mixing flow path owing to adiabatic expansion of the air by the spray nozzle and both the adiabatic expansion of the air by the spray nozzle and the collision-turbulent-flow movement of the mixed gas.

By providing a gas-and-liquid separator such as a mist separator and a drain catcher at the spray nozzle or the mixer, if mist whose particle is large is condensed and condensed mist is separated as water drops, by temperature lowering within the mixing flow path owing to collision-turbulent-flow movement of the mixed gas, then the water drops are separated from the released air, so that efficiency of the apparatus can be further enhanced.

Figure 8:
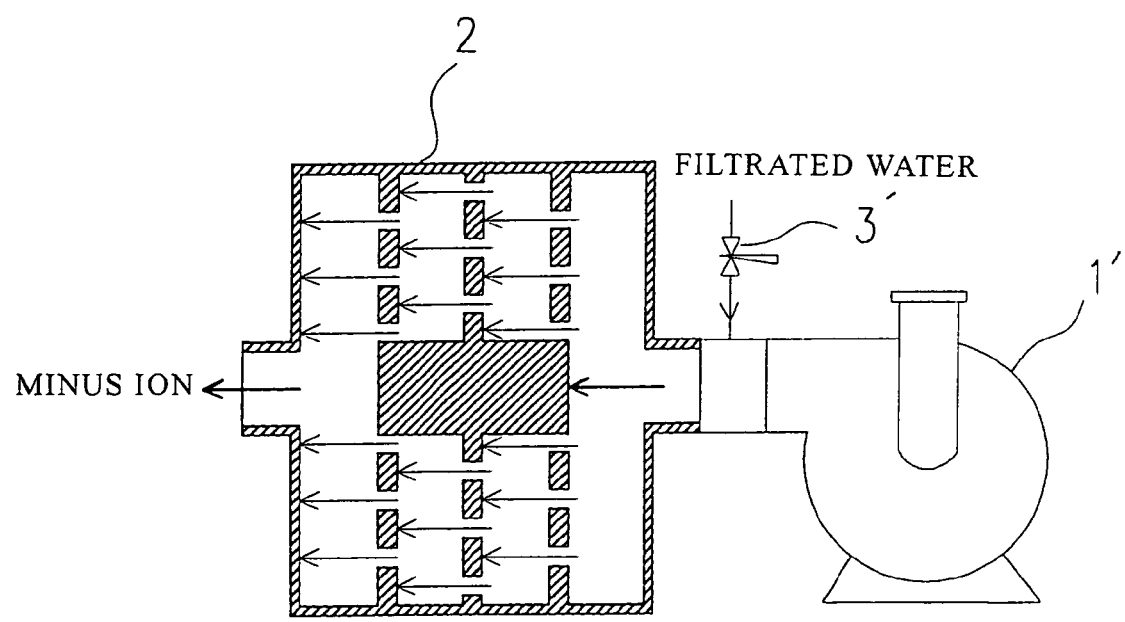
FIG. 8 is a schematic view of a minus ion generating apparatus in which a mixer and a blower are combined, minus ions are generated by supplying water.

FIG. 8 is a schematic view of a minus ion generating apparatus in which a mixing flow path and a blower are combined, minus ions are generated by supplying water.

Figure 9:
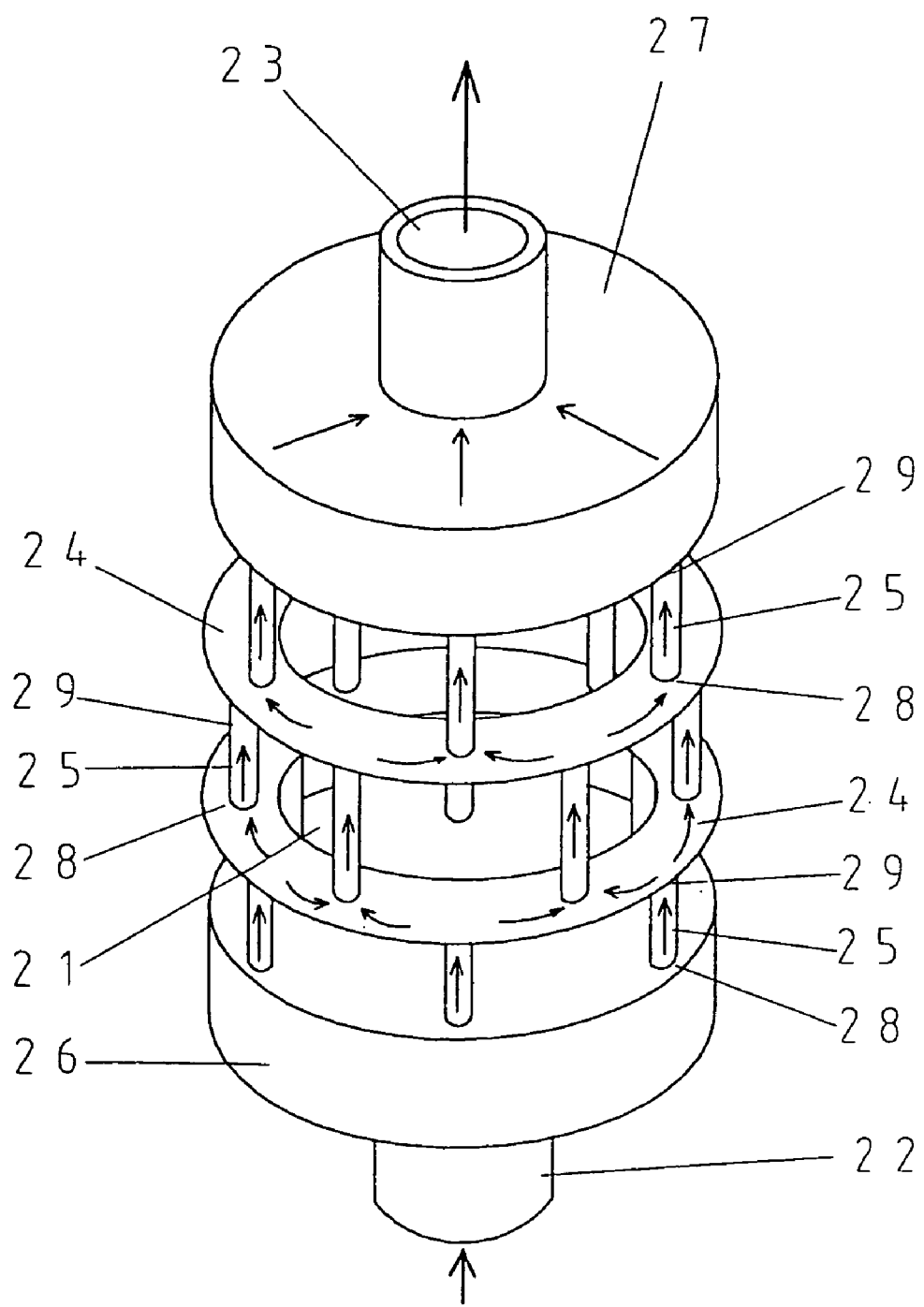
FIG. 9 is a perspective view in a case where a mixing flow path used for the apparatus in the embodiment of the present invention is made in a pipe manner.

FIG. 9 is a perspective view in a case where a mixing flow path used for the apparatus in one embodiment of the present invention are fabricated using pipes.

A mixer 2 of the present embodiment is constituted by a mixing flow path 21, a supplying flow path 22 that supplies a mixed gas of air and water to the mixing flow path 21, and a discharging flow path 23 for discharging as shown in FIG. 8. The mixing flow path 21 is constituted by circular flow paths 24, communicating flow paths 25, a tank 26 at a supplying side for introducing the mixed gas from the supplying flow path 22 to the communicating paths 25, and a tank 27 at an discharging side for introducing the mixed gas from the communicating flow paths 25 to the discharging flow path 23. A desired number of the circular flow paths may be one or more. A desired number of the communicating path may be two or more. In one embodiment of the present invention, the number of the circular flow paths is two and the number of the communicating flow paths is six.

Pipe members are, for example, made of metal, plastic, or the like.

A fan, a blower, a compressor and the like are used as a means that supplies a high-speed air to the flow paths.

A water supplying apparatus is provided before the flow paths in order to generate minus ions, so that a high-speed air and water are mixed and introduced thereto. There exists a water pump or the like that sends water by pressurizing water as an apparatus for supplying water. Water from the Water Bureau or the like which has been already pressurized may be used as it stands without any pump.

Further, a pressure difference owing to gravity of water is used, thereby water in a storage tank or the like lying above the supplying flow path may be transported.

Water is heated or made into mist by using ultrasonic wave and thereafter the misted water may be taken from the air entrance together with the air.

Preferably, an adjusting valve for water may be provided in order to effectively enhance a condition for generating minus ions.

A proper amount of water is mixed into the high-speed air to be transported to the flow paths by a blower 1' by way of an adjusting valve 3' for water. A mixed air of the high-speed air and water passes through the supplying flow path 22 and enters the tank 26 at the supplying side. The mixed air that mutually collided within the tank 26 passes through the inlets 28 of the plural communicating flow paths 25 and enters the circular flow path 24 at a first stage from the outlets 29. After that, the mixed air collides against a wall surface of the circular flow path 24 and further the mixed airs entered from different inlets mutually collide.

Likewise, the high-speed mixed air passes through the inlets 28 of plural communicating flow paths 25 connected to the circular flow path 24 at the first stage. Thereafter, the mixed air enters the circular flow path 24 at the second stage from the outlets 29 and collides against the wall surface of the circular flow path 24, and the mixed airs entered from different inlets mutually collide Next, the mixed air passes through the inlets 28 of plural communicating flow paths 25 connected to the circular flow path 24 at the second stage and thereafter enters the tank 27 from the outlets 29. The mixed air that has collided against an inner surface of the tank 27 is discharged from the discharging flow path 23.

Water in the air is finely broken, becomes fine mist and is scattered, when the water in the air collides against the inner wall surface of the tank 26. Then, hydrogen boding of water is broken and thereafter water becomes to be charged with minus charges. Further, the high-speed air collides against the wall surface at plural locations within the circular flow path 24, the high-speed air performs collision-turbulent-flow movement, so that water in the air is further more fined. Finally, the high-speed air collides against the inner surface of the tank 27. Here, a particle of the water has become very fine by plural times of collision-turbulent-flow movement, so that the minus ions become adhered to the particle of water. Therefore, the high-speed mixed air including minus ions is discharged from the discharging flow path 23.

The apparatus of the present embodiment can more efficiently generate a large amount of fined particles of water than the minus ion generating method of generating minus ions when water is scattered by only once falling in a fall. Therefore, the apparatus can generate a large amount of minus ions.

In a method of spraying water by only once falling in a fall, particles of water is large and there still exist a large number of plus ions. However, in the method of the present embodiment, most of water can be made into fine particles having minus ions, so that without generating plus ions, a large amount of minus ions can be continuously and stably generated and the minus ions can be adhered to a fine water particle.

The high-speed air used for generating the minus ions is discharged as they stand toward the available space and allows the minus ions to be spread over in wide space. Most of water can be made into fine particles, so that it is not necessary to circulate and recover the water, and there is no occurrence of drain and so on.

There is no fear that a harmful gas might be produced by dirty of the electrodes in case of the method employing the corona discharging. The water in the high-speed air is repeatedly made to be in collision-turbulent-flow movement within the mixer 2. As a result, the larger amount of minus ions can be effectively and safely generated than an amount of minus ions obtained by the "Lenard phenomenon" in the fall.

If the phenomenon that a particle of water is made to be fine is used and water including impurities such as seawater or the like is injected to the apparatus of the present embodiment, then the seawater is mixed with the air and is made to be fined, and water component is vaporized and separated from water component including impurities such as salt component. Thus, separation can be established between the water and the impurities such as salt component that has been dissolved into the water.

As the other usage, if a medicine in a liquid manner or the like is transported in place of the water in a same manner, the medicine can be fined and scattered for a short time toward the atmosphere in an even state, so that a space of a room can be also sterilized for a short time.

Figure 10:
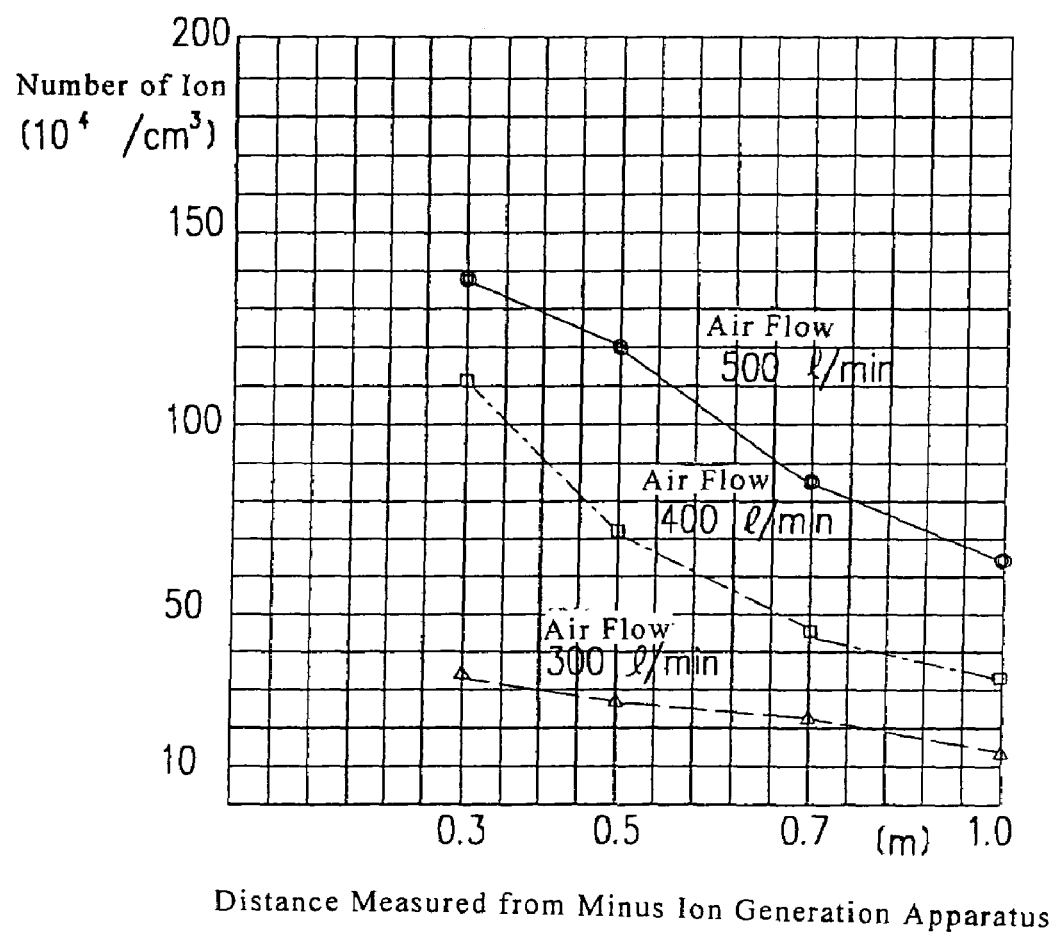
FIG. 10 is a graph representing an experimental result of an amount of minus ions generated using the minus ion generating apparatus in one embodiment of the present invention.

Through the above-mentioned constitution, according to the present embodiment, a splendid performance can be attained as shown in a graph of FIG. 10.

In the performed experiment, when a constant amount of water by the pump whose speed was 0.1 [liter/hour] was mixed to the pressurized air by the compressor, at a location where the distance from the discharging flow path 23 of the minus ion generating apparatus was 1 [meter], minus ions were generated by 640,000 [ions/cm$^3$], in case where a flow amount of the air was 500 [liter/min]. This number meets the International Ionization Standard (in which the number of minus ions is 100,000 or more [ions/cm$^3$] at a location where the distance from the minus ion generating apparatus was 1 [meter]).

In the above mentioned embodiment, the mixing flow path shown in FIG. 4 that is made in a block manner can be used.

INDUSTRIAL APPLICABILITY

As above-mentioned, the minus ion generating apparatus, the minus ion generating system, and the minus ion generating method according to the present invention are useful as the minus ion generating apparatus, the minus ion generating system, and the minus ion generating method on various kind of purposes, which are suitable to be used in the inside of a room, especially at home.

The invention claimed is:

1. A minus ion generating apparatus comprising:
    a mixing flow path comprising;
        plural circular flow paths that are arranged in parallel and that are communicated in a radial direction,
        plural inlets and plural outlets formed in said circular flow paths so that the location of the inlets and the location of the outlets are mutually different in a radial direction in each of said circular flow paths, and
        plural communicating flow paths by which the inlet formed in one circular flow path communicates with the outlet formed in another circular flow path,
    a supplying flow path for fluid which communicates with the mixing flow path, and
    a discharging flow path for fluid which communicates with the mixing flow path.

2. The minus ion generating apparatus according to claim 1, wherein a tank is connected to said supplying flow path.

3. The minus ion generating apparatus according to claim 1 or 2, wherein a tank is connected to said discharging flow path.

4. The minus ion generating apparatus according to claim 1, in which a spray nozzle is connected to said supplying flow path.

5. The minus ion generating apparatus according to claim 1, in which a gas-and-liquid separator is connected to said discharging flow path.

6. The minus ion generating apparatus according to claim 1, wherein a device for supplying air is connected to the minus ion generating apparatus.

7. The minus ion generating apparatus according to claim 1, or 6, wherein a device for supplying water is connected to the minus ion generating apparatus.

8. A minus ion generating system wherein the minus ion generating apparatus according to claim 1, are connected to a pipe for sending wind in a single system manner at plural locations.

9. A minus ion generating method for generating minus ions by sending water and air to the minus ion generating apparatus according to claim 1.

* * * * *